(12) United States Patent
Belzer et al.

(10) Patent No.: US 6,884,886 B2
(45) Date of Patent: Apr. 26, 2005

(54) PROCESS FOR PREPARING 6-ARYL-4H-S-TRIAZOLO[3,4-C]-THIENO[2,3-E]-1,4-DIAZEPINES

(75) Inventors: Werner Belzer, St. Goar (DE); Ralf Lock, Mainz (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 259 days.

(21) Appl. No.: 10/096,809

(22) Filed: Mar. 13, 2002

(65) Prior Publication Data

US 2002/0147190 A1 Oct. 10, 2002

Related U.S. Application Data

(60) Provisional application No. 60/289,880, filed on May 9, 2001.

(30) Foreign Application Priority Data

Apr. 4, 2001 (DE) .......................... 101 16 378

(51) Int. Cl.⁷ ............................. C07D 513/00
(52) U.S. Cl. ....................................... 540/560
(58) Field of Search ........................... 540/560

(56) References Cited

U.S. PATENT DOCUMENTS 3,840,558 A  10/1974 Nakanishi et al. ....... 260/329.5
4,094,984 A  6/1978 Weber et al. ............ 424/269
4,201,712 A  5/1980 Weber et al. ............ 260/244.4

*Primary Examiner*—Brenda Coleman
(74) *Attorney, Agent, or Firm*—Michael P. Morris; Mary-Ellen M. Devlin; Thomas Blankinship

(57) ABSTRACT

An improved process for preparing 6-aryl-4H-s-triazolo[3,4-c]-thieno[2,3-e]-1,4-diazepines of formula I,

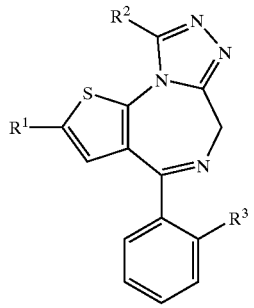

(I)

wherein:

$R^1$ is a hydrogen or halogen atom or a $C_1$–$C_6$ alkyl group, $R^2$ is a hydrogen or halogen atom or a $C_1$–$C_6$ alkyl, $C_1$–$C_6$ hydroxyalkyl, $C_3$–$C_6$ cycloalkyl group or a 5- or 6-membered oxygen-, sulphur- or nitrogen-containing heterocyclic group which may optionally be substituted at the nitrogen atom by a $C_1$–$C_3$ alkyl group, and $R^3$ is a hydrogen or halogen atom.

9 Claims, No Drawings

PROCESS FOR PREPARING 6-ARYL-4H-S-TRIAZOLO[3,4-C]-THIENO[2,3-E]-1,4-DIAZEPINES

RELATED APPLICATIONS

Benefit of U.S. Provisional Application Ser. No. 60/289,880, filed on May 9, 2001, is hereby claimed.

FIELD OF THE INVENTION

The invention relates to a process for preparing 6-aryl-4H-s-triazolo[3,4-c]-thieno[2,3-e]-1,4-diazepines of formula I,

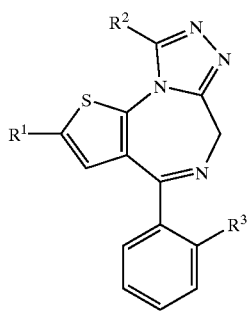

wherein $R^1$, $R^2$ and $R^3$ have the meanings given, from a 5-aryl-1,3-dihydrothieno[2,3-e]-1,4-diazepin-2-one of formula II

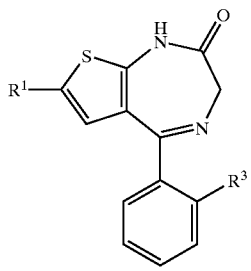

BACKGROUND OF THE INVENTION

6-Aryl-4H-s-triazolo[3,4-c]-thieno[2,3-e]-1,4-diazepines, particularly brotizolam ($R^1$=Br, $R^2$=methyl, $R^3$=Cl), are known for example from U.S. Pat. No. 4,094,984 and are valuable medicaments which have sedative properties, in particular, and may be used for treating sleep disorders.

However, the preparation described therein, starting from a 5-aryl-1,3-dihydrothieno[2,3-e]-1,4-diazepin-2-one of formula II, is unsuitable for production on an industrial scale, as the intermediate products involved, such as for example 5-aryl-1,3-dihydrothieno[2,3-e]-1,4-diazepin-2-thiones, have to be isolated, and when reacted give off foul-smelling and in some cases toxic thiols which may lead to contamination of the products.

The aim of the present invention is therefore to provide a process which makes it possible to synthesise, work up, purify and isolate 6-aryl-4H-s-triazolo[3,4-c]-thieno[2,3-e]-1,4-diazepines of formula I on an industrial scale while overcoming the disadvantages mentioned above.

DETAILED DESCRIPTION OF THE INVENTION

Surprisingly, it has been found that 6-aryl-4H-s-triazolo[3,4-c]-thieno[2,3-e]-1,4-diazepines of formula I, wherein
$R^1$ denotes a hydrogen or halogen atom or a $C_1$–$C_6$ alkyl group,
$R^2$ denotes a hydrogen or halogen atom or a $C_1$–$C_6$ alkyl, $C_1$–$C_6$ hydroxyalkyl, $C_3$–$C_6$ cycloalkyl group or a 5- or 6-membered oxygen-, sulphur- or nitrogen-containing heterocyclic group which may optionally be substituted at the nitrogen atom by a $C_1$–$C_3$ alkyl group, and
$R^3$ denotes a hydrogen or halogen atom, can be produced on an industrial scale if a 5-aryl-1,3-dihydrothieno[2,3-e]-1,4-diazepin-2-one of formula II,
wherein $R^1$ and $R^3$ are as herein defined,
(a) is treated with a chlorinating agent,
(b) the resulting 5-aryl-2-chlorothieno[2,3-e]-1,4-diazepine of formula III,

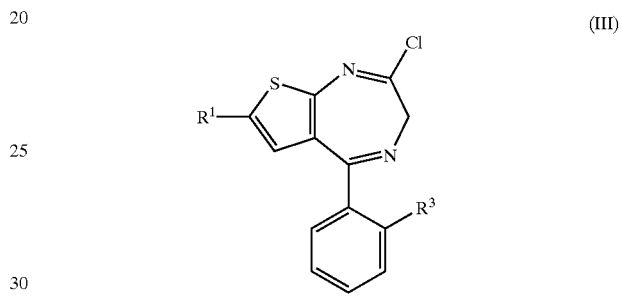

wherein $R^1$ and $R^3$ are as herein defined, is reacted with an acylhydrazine of formula IV

$R^2$—CO—NH—NH$_2$ wherein $R^2$ is as hereinbefore defined, and
(c) the product thus obtained is treated with a base.

The invention thus relates to a process for preparing the compounds of formula I from compounds of formula II according to steps (a), (b) and (c) mentioned above.

The invention also relates to a process for preparing a compound of formula I wherein $R^1$ denotes bromine, in which a compound of formula V,

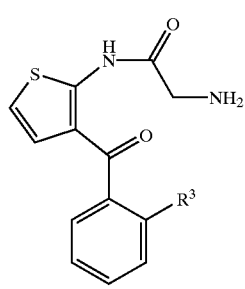

wherein $R^3$ is as hereinbefore defined,
is subjected to the following reactions one after another:
(d) cyclisation under water-cleaving conditions;
(e) reacting the product obtained in step d) with a brominating agent;
(f) converting the compound of formula II thus obtained wherein $R^1$ denotes bromine into the compound of formula I according to steps (a) to (c), characterised in that steps (d) and (e) are carried out in a one-pot process.

The invention also relates to 5-aryl-2-chlorothieno[2,3-e]-1,4-diazepines of formula III,

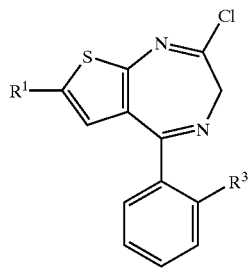

(III)

wherein R¹ and R³ have the meanings given, particularly 7-bromo-5-(2-chlorophenyl)-2-chlorothieno[2,3-e]-1,4-diazepine.

The term "alkyl" as used hereinbefore and hereinafter with regard to the groups R¹ and/or R² denotes a straight-chain or branched alkyl group with up to 6 C atoms, preferably 1 to 4 C atoms. Particularly preferred are methyl, ethyl, n-propyl, i-propyl, n-butyl and tert-butyl, particularly methyl.

The term "hydroxyalkyl" as used hereinbefore and hereinafter with regard to the group R² denotes a straight-chain or branched alkyl group with up to 6 C atoms, preferably 1 to 4 C atoms, which is substituted by a hydroxy group. ω-Hydroxyalkyl groups with 1 to 3 C atoms, particularly hydroxymethyl, 2-hydroxyethyl and 3-hydroxypropyl are preferred.

The term "cycloalkyl" as used hereinbefore and hereinafter with regard to the group R² denotes a cyclic alkyl group with 3 to 6 C atoms, preferably 5 or 6 C atoms, particularly cyclopentyl and cyclohexyl.

The term "heterocyclic group" as used hereinbefore and hereinafter with regard to the group R² denotes a saturated or unsaturated 5- or 6-membered heterocyclyl group, which contains in addition to carbon atoms and at least one heteroatom selected from among nitrogen, oxygen and sulphur. The following heterocyclyl groups are preferred: saturated or aromatic 5- or 6-membered heterocyclyl groups which contain one or two nitrogen atoms, particularly pyrrolidyl, pyrazolyl, imidazolyl, pyridyl, pyrimidyl, piperidyl and piperazyl, or a nitrogen atom and an oxygen or sulphur atom, particularly morpholino and thiomorpholino, contain an oxygen atom, particularly tetrahydropyranyl and tetrahydrofuranyl.

The term "one-pot process" as used hereinbefore and hereinafter for the sequence of certain reaction steps denotes the succession of two or more synthesis steps occurring one after another, with the intermediate product obtained in a first or second synthesis step being used in the next synthesis step without any isolation or purification. Preferably, the subsequent reaction step is carried out in the same reaction vessel and optionally in the presence of the reaction medium in which the previous reaction step was carried out.

In a preferred embodiment the groups R¹ to R³ have the following meanings:

R¹ denotes halogen or methyl, particularly bromine,
R² denotes hydrogen or methyl, particularly methyl, and
R³ denotes halogen, particularly chlorine.

In a preferred embodiment of the process according to the invention for preparing the compound of formula I:

in step (a) the compound of formula (II) is reacted with phosphorus pentachloride in the presence of an inert diluent and a tertiary amine;

in step (b) the compound of formula (III) is reacted at a temperature below 100° C. with acetic acid hydrazide in the presence of an inert diluent.

in step (c) the compound obtained in step (b) is treated with aqueous sodium hydroxide solution at a temperature of 0° C. to 50° C.;

the reaction sequence of steps (a) to (c) is carried out in a one-pot process.

Stage II→III
Step (a)

The reaction of the compound of formula II with the chlorinating agent is generally carried out in the presence of an inert diluent.

Preferably the compound of formula II is reacted with a chlorinating agent selected from among thionyl chloride, sulphuryl chloride, titanium tetrachloride, oxalyl chloride, phosgene, di- and triphosgene, phosphorus trichloride, phosphorus oxychloride, phosphorus pentachloride and antimony pentachloride, conveniently in a diluent such as tetrahydrofuran, dioxane, toluene, dichloromethane, chloroform or chlorobenzene, or mixtures of these diluents, optionally in the presence of an organic base, e.g. triethylamine, N-ethyldiisopropylamine, pyridine or 4-dimethylaminopyridine, at temperatures from –20 to +60° C., preferably –10 to +20° C. The reaction is generally carried out at normal pressure, using 0.9 to 2.0, preferably 1.1 to 1.9, particularly 1.2 to 1.4 mol of a chlorinating agent based on 1 mol of the compound of formula II. The reaction is generally complete, under the conditions specified, after 15 to 600 minutes, preferably 30 to 180 minutes. The crude product obtained is generally further processed in the next step without any other purification.

In a particularly preferred embodiment of the process according to the invention a suspension of the compound of formula II in pyridine and dichloromethane is added dropwise to a suspension of 1.1 to 1.5 mol of phosphorus pentachloride based on 1 mol of the compound of formula II in dichloromethane at 0 to 20° C. with cooling. The mixture is stirred for 30 to 120 minutes at about 10° C.

Stage III→I
Step (b)

The reaction of the compound of formula III with the compound of formula IV generally takes place in an inert solvent.

Preferably, the compound of formula III is reacted with a compound of formula IV, particularly acetic acid hydrazide, conveniently in a diluent such as tetrahydrofuran, dioxane, toluene, dichloromethane, chloroform or chlorobenzene, or mixtures of these diluents, particularly in a mixture of dichloromethane and tetrahydrofuran, optionally in the presence of an organic base, e.g. triethylamine, N-ethyldiisopropylamine, pyridine or 4-dimethylaminopyridine, and the other reaction products formed in step (a), e.g. phosphorus oxychloride, at temperatures from 0 to 100° C., preferably 10 to +90° C. The reaction is generally carried out at normal pressure, using 0.9 to 3.0, preferably 1.5 to 2.5, particularly 1.8 to 2.2 mol of a compound of formula IV based on 1 mol of the compound of formula III. The reaction is generally complete, under the conditions specified, after 1 to 48 hours, preferably 5 to 24 hours. The crude product obtained is generally further processed in the next step without any other purification.

In a particularly preferred embodiment of the process according to the invention, a heated solution of about 2 equivalents of acetic acid hydrazide in tetrahydrofuran based on 1 equivalent of formula III is added dropwise with cooling at 0–30° C. to the reaction mixture obtained in step (a). The resulting mixture is then stirred for a further 0.5 to 2 hours at ambient temperature and then refluxed for 5–20 hours. The brotizolam is obtained as the hydrochloride/ phosphate, and the brotizolam is liberated by the subsequent addition of a base.

Step (c)

The reaction of the compound obtained in step (b) with the base generally takes place in the presence of an inert solvent.

Preferably, the compound obtained in step (b) is reacted with an aqueous base, particularly sodium hydroxide, conveniently in a diluent such as water, methanol, ethanol, tetrahydrofuran, dioxane, toluene, dichloromethane, chloroform, acetone, methylethylketone or chlorobenzene, or mixtures of these diluents, particularly in a mixture of dichloromethane, tetrahydrofuran and water, optionally in the presence of an organic base, e.g. triethylamine, N-ethyldiisopropylamine, pyridine or 4-dimethylaminopyridine and the other reaction products obtained in steps (a) and (b), e.g. phosphorus oxychloride, at temperatures from 0 to 120° C., preferably 10 to 100° C. The reaction is generally carried out at normal pressure using 1.0 to 10, preferably 6 to 9 mol of a base, based on 1 mol of the chlorinating reagent. The reaction is generally complete, under the conditions specified, after a few minutes to several hours, 0.1 to 24 hours, preferably 0.1–2 h. The crude product obtained is generally isolated by extraction and/or crystallisation and optionally purified by recrystallisation.

In a particularly preferred embodiment of the process according to the invention water is added to the reaction mixture obtained in step (b), with cooling, and the pH is adjusted with sodium hydroxide solution to an alkaline level of 7.5–13, particularly 9–11. The phases are separated and the aqueous phase is extracted with dichloromethane. The combined organic phases are preferably decolorised with activated charcoal, filtered and evaporated to dryness in vacuo. The residue is taken up in boiling methylethylketone, decolorised again, filtered and then evaporated down. The mixture is cooled to 0 to 10° C. and stirred for a further 2 hours at this temperature. The product that crystallises out is filtered off, washed with methylethylketone and ethyl acetate and dried.

In a preferred embodiment of the process according to the invention for preparing the compound of formula II:

the compound of formula V is heated in step (d) with an acid in a high-boiling solvent;

the compound obtained in step (d) is reacted with bromine in the presence of a tertiary amine.

Stage V→II

Step (d)

The cyclising of the compound of formula V generally takes place in the presence of an inert diluent.

Preferably, the compound of formula V is reacted with an acid selected from among hydrochloric acid, sulphuric acid, p-toluenesulphonic acid, phosphoric acid, a carboxylic acid such as acetic acid, propionic acid, pivalic acid, trifluoroacetic acid and silica gel, optionally in the presence of a base such as pyridine, conveniently in a high-boiling diluent such as n-butanol, amylalcohol, toluene, xylene, chlorobenzene, or mixtures of these diluents at temperatures from 20 to 160° C., preferably 60 to 140° C. The reaction is generally carried out at normal pressure using 1.5 to 6.0, preferably 1.9 to 4.0, particularly 3.2 to 3.8 mol of an acid, based on 1 mol of the compound of formula V. The reaction is generally complete, under the conditions specified, after 15 to 600 minutes, preferably 30 to 180 minutes. The crude product obtained is generally further processed in the next step without any other purification.

In a particularly preferred embodiment of the process according to the invention, one part of 2-amino-N-[3-(2-chlorobenzoyl)thiophen-2-yl]acetamide is added to a mixture of 4 to 12 parts of n-butanol and 0.4 to 1.2 parts of glacial acetic acid at 80–110° C. and refluxed for 0.5 to 2 hours.

Step (e)

The reaction of the compound obtained in step (d) with a brominating agent generally takes place in the presence of an inert solvent.

Preferably, the compound obtained in step (d) is reacted with a brominating agent selected from among bromine, N-bromosuccinimide and 1,3-dibromo-5,5-dimethylhydantoin, conveniently in a diluent such as n-butanol, amylalcohol, toluene, xylene, chlorobenzene, or mixtures of these diluents, optionally in the presence of an organic base, e.g. triethylamine, N-ethyldiisopropylamine or pyridine, at temperatures from −20 to +60° C., preferably −10 to +20° C. The reaction is generally carried out at normal pressure, using 0.9 to 2.0, preferably 1.1 to 1.9, particularly 1.2 to 1.8 mol of a brominating agent based on 1 mol of the compound of formula V. The reaction is generally complete, under the conditions specified, after 15 to 600 minutes, preferably 30 to 240 minutes. The crude product obtained is generally isolated by crystallisation and optionally purified by recrystallisation.

In a particularly preferred embodiment of the process according to the invention the reaction mixture obtained in step (d) is cooled to ambient temperature, and pyridine and about 1.2 to 1.8 mol bromine based on 1 mol of the compound of formula V used are added. The resulting mixture is then stirred for a further 0.1 to 4 hours, cooled to 0–20° C. and stirred for another 1 to 3 hours at this temperature. The product that crystallises out is isolated by filtration, washed with aqueous ethanol and dried.

The compound of formula V needed as a starting material is known, for example, from published German application DE 22 17 157 or U.S. Pat. No. 4,094,984 and can be prepared in a manner known per se by reacting a 2-amino-3-arylthiophene with bromoacetylbromide and ammonia.

Other advantageous aspects of the method according to the invention are the high space/time yields of the present process and the high yield and purity of the associated intermediate products, which can be further processed without being purified by chromatography.

The Examples that follow serve to illustrate the processes carried out by way of example for preparing the compound of formula I. They are to be understood as being possible methods given solely as examples without restricting the invention to their content.

EXAMPLE 1

7-Bromo-5-(2-chlorophenyl)-1,3-dihydrothieno[2,3-e]-1,4-diazepine-2-one, (1)

220 g (0.746 mol) of 2-amino-N-[3-(2-chlorobenzoyl)thiophen-2-yl]acetamide (prepared by reacting 2-amino-3-(2-chlorobenzoyl)thiophene with bromoacetylbromide and subsequently piping in gaseous ammonia) are added at 110° C. to a mixture of 1.8 l of n-butanol and 150 ml of glacial acetic acid. The mixture is refluxed for 1 hour, cooled to ambient temperature and 330 ml of pyridine and 57 ml (178.8 g, 1.12 mol) of bromine are added with cooling. Then the mixture is stirred for another 0.5 to 2 hours, cooled to 5 to 10° C. and stirred for a further 2 hours at this temperature. The product that crystallises out is isolated by filtration, washed with 50% ethanol and dried overnight in vacuo at 60° C.

Yield: 152 g (57.3%).

EXAMPLE 2

Brotizolam

A suspension of 50 g (0.14 mol) of (1) in 2.5 ml of pyridine and 200 ml of dichloromethane is added dropwise to a suspension of 36 g (0.183 mol) of phosphorus pentachloride in 250 ml of dichloromethane at 5–10° C. with cooling. The mixture is stirred for 1 hour at 10° C. and a solution of 17 g (0.28 mol) of acetic acid hydrazide in 170 ml of tetrahydrofuran, heated to 40–50° C., is added dropwise with cooling at 10–20° C. The mixture is then stirred for 1 hour at ambient temperature and then refluxed for 5 to 18 hours. It is then cooled to ambient temperature, 380 ml water are added with cooling and the mixture is adjusted to an alkaline pH with 45% sodium hydroxide solution. The phases are separated and the aqueous phase is extracted with 100 ml of dichloromethane. 5 g of activated charcoal are added to the combined organic phases which are then stirred for 10 minutes, filtered and evaporated to dryness in vacuo. The residue is taken up in 750 ml of boiling methylethylketone, 5 g of activated charcoal are added and the resulting mixture is refluxed for another 10 min. The suspension is filtered, then 570 ml of solvent are distilled off. The mixture is allowed to cool slowly to ambient temperature and then cooled to 5° C. and stirred for 2 hours at this temperature. The product that crystallises out is filtered off, washed with 30 ml of cold methylethylketone and 50 ml of cold ethyl acetate and dried overnight at 60° C. in vacuo. Yield: 36.6 g (66%) of brotizolam.

What is claimed is:

1. A process for preparing a 6-aryl-4H-s-triazolo[3,4-c]-thieno [2,3-e]-1,4-diazepine of the formula I,

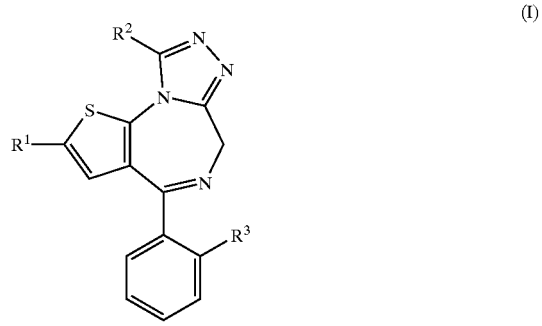

wherein
  $R^1$ denotes a hydrogen or halogen atom or a $C_1$–$C_6$ alkyl group,
  $R^2$ denotes a hydrogen or halogen atom or a $C_1$–$C_6$ alkyl, $C_1$–$C_6$ hydroxyalkyl, $C_3$–$C_6$ cycloalkyl group or a 5- or 6-membered oxygen-, sulphur- or nitrogen containing heterocyclic group which may optionally be substituted at the nitrogen atom by a $C_1$–$C_3$ alkyl group, and
  $R^3$ denotes a hydrogen or halogen atom,
in which process,
  (a) a 5-aryl-1,3-dihydrothieno[2,3-e]-1,4-diazepine-2-one of the formula II

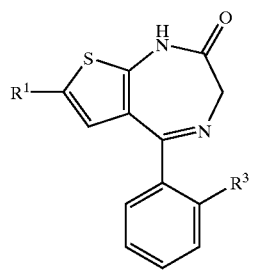

wherein $R^1$ and $R^3$ are as herein defined, is treated with a chlorinating agent, to produce a corresponding 5-aryl-2-chlorothieno[2,3-e]-1,4-diazepine of the formula III

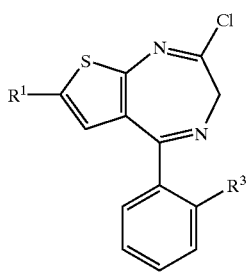

wherein $R^1$ and $R^3$ are as herein defined,
  (b) the 5-aryl-2-chlorothieno[2,3-e]-1,4-diazepine of the formula III thus obtained is reacted with an acylhydrazine of the formula IV

R2—CO—NH—NH2        (IV)

wherein $R^2$ is as hereinbefore defined, and
  (c) the compound obtained in step (b) is treated with a base.

2. The process according to claim 1 for preparing a compound of the formula I, wherein $R^1$ denotes a bromine atom, $R^2$ denotes a methyl group and $R^3$ denotes a chlorine atom.

3. The process according to claim 1, wherein steps (a) to (c) are carried out in a one-pot process.

4. The process according to claim 1, wherein in step (a) the compound of the formula (II) is reacted with phosphorus pentachloride in the presence of an inert diluent and a tertiary amine.

5. The process according to claim 1, wherein in step (b) the compound of the formula (III) is reacted with acetic acid hydrazide at a temperature below 100° C. in the presence of an inert diluent.

6. The process according to claim 1, wherein in the step (c) the compound obtained in step (b) is treated with aqueous sodium hydroxide solution at a temperature from 0° C. to 50° C.

7. A process for preparing a compound of the formula I,

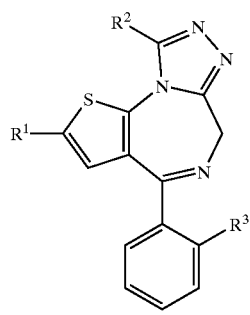

(I)

wherein
$R^1$ denotes bromine,
$R^2$ denotes a hydrogen or halogen atom or a $C_1$–$C_6$alkyl, $C_1$–$C_8$ hydroxyalkyl, $C_3$–$C_6$ cycloalkyl group or a 5- or 6-membered oxygen-, sulphur- or nitrogen-containing heterocyclic group which may optionally be substituted at the nitrogen atom by a $C_1$–$C_3$ alkyl group, and
$R^3$ denotes a hydrogen or halogen atom.
in which process;
(a) a compound of the formula V

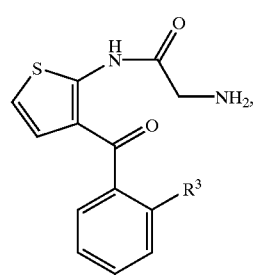

(V)

wherein $R^3$ is as hereinbefore defined, is cyclized, by the removal of water, to yield an intermediate of the formula II

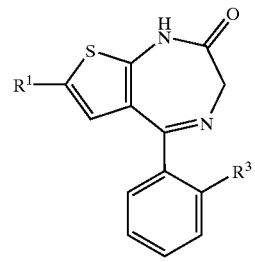

(II)

wherein $R^1$ is hydrogen and $R^3$ is as hereinbefore defined:

(b) the intermediate of the formula II produced in step (a) is treated with a brominating agent to produce an intermediate of the formula II wherein $R^1$ is bromine;

(c) the brominated intermediate of the formula II produced in step (b) is treated with a chlorinating agent, to produce a corresponding 5-aryl-2-chlorothieno[2,3-e]-1,4-diazepine of the formula III

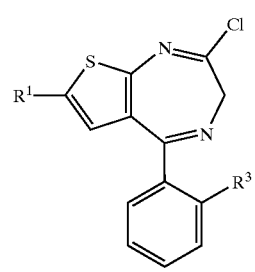

(III)

wherein $R^1$ is bromine and $R^3$ is as hereinbefore defined;

(d) the 5-aryl-2-chlorothieno[2,3-e]-1,4-diazepine of the formula III thus obtained is reacted with an acylhydrazine of the formula IV

R2-CO—NH—NH2    (IV)

wherein $R^2$ is as hereinbefore defined, and (e) the product of step (d) obtained is treated with a base to yield the product of the formula I, wherein steps (a) and (b) are carried out in a single pot.

8. The process according to claim 7, wherein the compound of formula V is heated in step (a) with an acid in a high-boiling solvent.

9. The process according to claim 7, wherein the compound obtained in step (a) is reacted with bromine in the presence of a tertiary amine.

* * * * *